(12) United States Patent
Linton et al.

(10) Patent No.: US 11,389,414 B2
(45) Date of Patent: Jul. 19, 2022

(54) METHODS FOR TREATING ATHEROSCLEROSIS WITH GAMMA-KETOALDEHYDE SCAVENGERS

(71) Applicant: Vanderbilt University, Nashville, TN (US)

(72) Inventors: Macrae F. Linton, Nashville, TN (US); John A. Oates, Nashville, TN (US); Sean S. Davies, Nashville, TN (US); L. Jackson Roberts, II, Gallatin, TN (US); Venkataraman Amarnath, Brentwood, TN (US); Patricia G. Yancey, Nashville, TN (US); Huan Tao, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 16/607,700

(22) PCT Filed: Apr. 27, 2018

(86) PCT No.: PCT/US2018/029999
§ 371 (c)(1),
(2) Date: Oct. 23, 2019

(87) PCT Pub. No.: WO2018/201074
PCT Pub. Date: Nov. 1, 2018

(65) Prior Publication Data
US 2020/0138747 A1    May 7, 2020

Related U.S. Application Data

(60) Provisional application No. 62/491,225, filed on Apr. 27, 2017.

(51) Int. Cl.
*A61K 31/00* (2006.01)
*A61K 31/135* (2006.01)
*A61P 9/10* (2006.01)

(52) U.S. Cl.
CPC .............. *A61K 31/135* (2013.01); *A61P 9/10* (2018.01)

(58) Field of Classification Search
CPC .............................. A61K 31/135; A61P 9/10
See application file for complete search history.

(56) References Cited

FOREIGN PATENT DOCUMENTS

| JP | 2014-52491 A | 9/2014 |
|---|---|---|
| JP | 2020-517721 | 6/2020 |
| WO | WO00/21516 A2 | 4/2000 |
| WO | WO02/36109 A2 | 5/2002 |
| WO | WO03/011808 A1 | 2/2003 |
| WO | WO 2013/010034 A2 | 1/2013 |
| WO | WO2015009977 A1 | 1/2015 |
| WO | WO 2018/201074 | 1/2018 |
| WO | WO18/048932 A1 | 3/2018 |

OTHER PUBLICATIONS

Karin A. Jandeleit-Dahm et al., Advanced Glycation End Products in Diabetes-Associated Atherosclerosis and Renal Disease: Interventional Studies, Annals of the New York Academy of Sciences, vol. 1043, No. 1, Jun. 1, 2005, pp. 759-766.

*Primary Examiner* — Sikarl A Witherspoon
(74) *Attorney, Agent, or Firm* — Stites & Harbison PLLC; Richard S. Myers, Jr.

(57) ABSTRACT

A method of treating atherosclerosis, comprising administering to a patient in need there of an effective gamma-ketoaldehyde scavenging amount of a gamma-ketoaldehyde scavenging compound.

5 Claims, 7 Drawing Sheets

METHODS FOR TREATING ATHEROSCLEROSIS WITH GAMMA-KETOALDEHYDE SCAVENGERS

RELATED APPLICATIONS

This application claims priority from International Patent Application No. PCT/US2018/029999, filed Apr. 27, 2018, which claims priority from U.S. Provisional Application Ser. No. 62/491,225 filed Apr. 27, 2017, the entire disclosures of which are incorporated herein by this reference.

GOVERNMENT SUPPORT

This invention was made with government support under HL116263, awarded by the National Institutes of Health. The government has certain rights in the invention.

FIELD OF THE INVENTION

The present invention relates generally to the field of treating and preventing inflammation, and more specifically to the field of controlling isoketals and neuroketals.

The present invention also relates to the field of treating and preventing atherosclerosis or plaque buildup in arteries, the underlying cause of heart attack, stroke and peripheral vascular disease, and more specifically treating and preventing the development of atherosclerosis and cardiovascular events by controlling reactive aldehydes, including malondialdehyde (MDA), isoketals and neuroketals, and the damage they cause to lipoproteins (LDL and HDL) and the artery wall.

SUMMARY OF THE INVENTION

Lipid peroxidation produces oxidative stress and inflammation and accelerates the pathogenesis of atherosclerosis and cardiovascular events. The ability of the aldehyde scavenger 2-hydroxybenzylamine (2-HOBA) (salicylamine) to prevent the development of atherosclerosis and was examined in Ldlr$^{-/-}$ mice fed a western diet for 16 weeks. Compared to mice treated with vehicle or the nonreactive analogue, 4-HOBA, 2-HOBA treatment significantly decreased the development of atherosclerosis in hypercholesterolemic Ldlr$^{-/-}$ mice by 31% in the proximal aortas and 60% in en face aortas. Treatment with 2-HOBA did not impact plasma cholesterol levels but resulted in reduced aldehyde content in HDL, LDL, and in the atherosclerotic lesions. The western diet increased the plasma malondialdehyde (MDA)-apoAI adduct levels in Ldlr$^{-/-}$ mice. Importantly, 2-HOBA treatment reduced MDA-apoAI formation and increased the capacity of the mouse HDL to reduce macrophage cholesterol stores versus vehicle or 4-HOBA. In addition, 2-HOBA reduced in vivo formation of MDA-apoB adducts, and MDA scavenging with 2-HOBA during LDL modification reduced macrophage cholesterol accumulation in vitro. Furthermore, 2-HOBA reduced macrophage death and inflammation in response to oxidative stress. Importantly, 2-HOBA treatment reduced the number of atherosclerotic lesion TUNEL positive cells by 72% and increased the number of dead cells that were phagocytosed compared to 4-HOBA or vehicle treated mice. This promoted stable plaque formation in 2-HOBA treated mice as evidenced by the 69% (p<0.01) reduction in necrotic core and by the increased collagen content (2.7-fold) and fibrous cap thickness (2.1-fold). The present invention shows that aldehyde scavenging with 2-HOBA has multiple atheroprotective effects on lipoproteins and reduces atherosclerosis in murine models. Accordingly, one embodiment of the present invention is a novel therapeutic approach for the prevention and treatment of atherosclerotic cardiovascular disease.

Thus, one aspect of the present invention is a method of treating, preventing, or ameliorating atherosclerosis, comprising administering to a patient in need thereof a compound of the following formula:

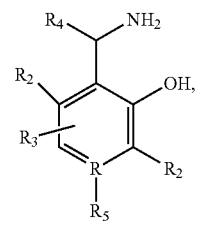

wherein:
R is N or C;
$R_2$ is independently H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_2$, $R_3$ and $R_4$, and may cyclize with to one or more $R_2$, $R_3$, or $R_5$ to form an optionally substituted $C_{3-8}$ membered ring containing C, O, S or N;
$R_3$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$ or $R_5$ to form an optionally substituted $C_{3-8}$ membered ring containing C, O, S or N;
$R_4$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_5$ to form an optionally substituted $C_{3-8}$ membered ring containing C, O, S or N;
$R_5$ is a bond, H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N;
and stereoisomers and analogs thereof.

BRIEF DESCRIPTION OF THE FIGURES

(FIG. 1A and FIG. 1C) Representative images show Red-Oil-O stain in proximal aorta root sections (FIG. 1A) and in open-pinned aortas (FIG. 1C). (FIG. 1B and FIG. 1D) Quantitation of the mean Oil-Red-O stainable lesion area in aorta root sections (FIG. 1B) and en face aorta (FIG. D). N=9 or 10 per group,  p<0.01, * p<0.001. (FIG. 1E) The plasma total cholesterol and triglyceride levels. N=9 or 10 per group.

(FIG. 2A) Representative images show MDA staining (Red) in proximal aortic root sections. (FIG. 2B) Quantitation of the mean MDA positive lesion area in aortic root sections using ImageJ software. Data present as mean±SEM, N=6 per group, *** p<0.001.

(FIG. 3A) Representative images show Masson's Trichrome stain in aorta root sections. The collagen content (FIG. 3B), fibrous cap thickness (FIG. 3C), and necrotic area (FIG. 3D) were quantitated using ImageJ software. N=8 per group. * p<0.05, scale bar=100 µm. Blue shows collagen, Red, cytoplasm, Black, nuclei.

(FIG. 4A) Representative Images show dead cells that were detected by TUNEL staining (Red) of proximal aorta sections. Macrophages were detected by anti-macrophage primary antibody (green), and nuclei were counter stained with Hoechst (blue). (FIG. 4B) A representative image taken a higher magnification to indicate macrophage-associated TUNEL stain (yellow arrows) and white arrows indicate free dead cells that were not associated with macrophages. (FIG. 4C) Quantitation of the number of TUNEL-positive nuclei in proximal aortic sections. (FIG. 4D) Efferocytosis was examined by quantitating the free versus macrophage-associated TUNEL-positive cells in the proximal aortic sections. Data are indicated as mean±SEM (N=8 per group). Scale bar=50 µm, ** p<0.01.

(FIG. 5A and FIG. 5B) Mouse aortic endothelial cells (FIG. 5A) or primary macrophages (FIG. 5B) were incubated for 24 h with 250 µM $H_2O_2$ alone or with either 4-HOBA or 2-HOBA. Apoptotic cells were then detected by Annexin V staining and flow cytometry. (FIG. 5C, FIG. 5D, FIG. 5E, FIG. 5F, FIG. 5G, FIG. 5H) The mRNA levels of IL-1β, IL-6, and TNF-α were analyzed by real time PCR in the peritoneal macrophages incubated for 24 h with either oxidized LDL (FIG. 5C-FIG. 5E) or 250 µM $H_2O_2$ (FIG. 5F-FIG. 5H) alone or with either 4-HOBA or 2-HOBA. (FIG. 5A to FIG. 5H) Data present as mean±SEM from three independent experiments, *** p<0.001.

(FIG. 6B) LDL was modified in vitro with MDA in the presence of vehicle alone or with 2-HOBA, and then the LDL was incubated for 24 h with macrophages and the cellular cholesterol was measured. Data are representative of 3 independent experiments.

(FIG. 7A) The plasma levels of MDA-HDL adducts were measured by ELISA in $Ldlr^{-/-}$ mice treated as described in FIG. 6. Data present as mean±SEM (N=8 per group), *** p<0.001. (FIG. 7B) Western blots of apoAI and MDA-apoAI in mouse plasma after immunoprecipitation using primary anti-apoAI antibody. $Ldlr^{-/-}$ mice were treated as described in FIG. 6 and apoAI and MDA-apoAI from plasma of $Ldlr^{-/-}$ mice consuming a chow diet are included for comparison. (FIG. 7C) Quantitation using ImageJ software of the mean density (artificial units) of MDA-apoAI detected by Western blotting (FIG. 7B). (FIG. 7D) The HDL was isolated from the plasma of $Ldlr^{-/-}$ mice consuming a western diet for 16 weeks and treated with 2-HOBA or 4-HOBA or vehicle. Cholesterol enriched macrophages were incubated for 24 h with HDL (25 µg protein/ml), and the % reduction in cellular cholesterol content measured. The levels of HDL-MDA modification was analyzed by ELISA. Data present as mean±SEM, N=7 per group, * p<0.05, ** p<0.01. (FIG. 7E) Human HDL was modified with increasing doses of MDA, and then, the ability of the HDL to reduce the cholesterol content of cholesterol-enriched macrophages was measured. Data are representative of 3 independent experiments. (FIG. 7F) The plasma levels of MDA-HDL adducts were measured by ELISA in control or FH subjects before and after LA. (FIG. 7G) The capacity of HDL from control or FH subjects pre and post LA 9 (n=6 per group) to reduce the cholesterol content of $apoE^{-/-}$ macrophages.

DESCRIPTION OF THE INVENTION

Figure 1:
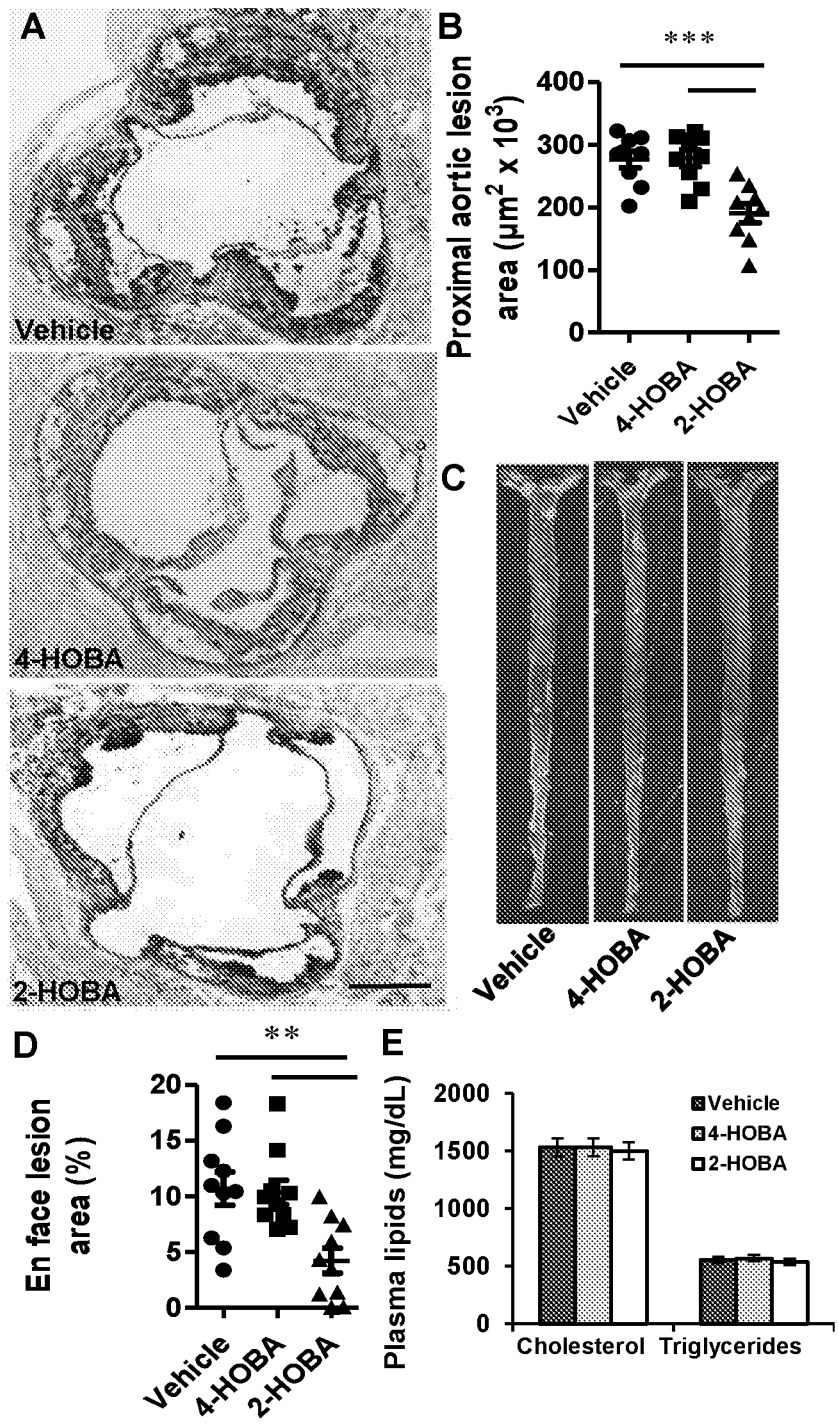
FIGS. 1A-1E show that an embodiment of the present invention, 2-HOBA, attenuates atherosclerosis in the hypercholesterolemic Ldlr$^{-/-}$ mice (a model of familial hypercholesterolemia). 8-week Ldlr$^{-/-}$ female mice were pretreated with 1 g/mL 2-HOBA or 1 g/mL 4-HOBA (nonreactive analogue) or vehicle (water) for 2 weeks and then the treatment was continued for 16 weeks during which the mice were fed a high-fat Western diet.

One embodiment of the present invention is a novel method of treating atherosclerosis.

Another embodiment of the present invention is methods of treating atherosclerosis by the administration of at least one compound of the present invention.

Another embodiment is a method for inhibiting atherosclerosis or atherosclerotic development in a mammal (e.g., a human), comprising administering an anti-atherosclerosis or anti-atherosclerotic development amount of a compound of the present invention as described herein, or a pharmaceutically acceptable salt thereof, to the mammal.

Another embodiment of the present invention is a compound or a pharmaceutically acceptable salt thereof for use as prophylactic or therapeutic treatment of atherosclerosis.

Another embodiment of the present invention is the use of a compound of the present invention or a pharmaceutically acceptable salt thereof to prepare a medicament for inhibiting atherosclerosis or atherosclerotic development in a mammal (e.g., a human).

Another embodiment of the present invention is the use of a compound of the present invention or a pharmaceutically acceptable salt thereof to prepare a medicament for inhibiting reactive aldehyde mediated damage of lipoproteins (including LDL and HDL) that promotes the development of atherosclerosis in a mammal (e.g., a human).

By "inhibition of atherosclerotic development" is meant the suppression of the development, progression and/or severity of atherosclerosis, a slowly progressive disease characterized by the accumulation of cholesterol within the arterial wall, e.g. by inhibiting, preventing or causing the regression of an atherosclerotic plaque.

Accordingly, the invention also provides a method for inhibiting atherosclerosis or atherosclerotic development in a mammal (e.g., a human), comprising administering an anti-atherosclerosis or anti-atherosclerotic development amount of a compound or composition of the present invention as described herein, or a pharmaceutically acceptable salt thereof, to the mammal.

Atherosclerosis, the underlying cause of heart attack and stroke, is the most common cause of death and disability in the industrial world. Elevated levels of apolipoprotein B (LDL and VLDL) containing lipoproteins and low levels of HDL increase the risk of atherosclerosis. Although lowering LDL with HMG-CoA reductase inhibitors has been shown to reduce the risk of heart attack and stroke in large outcomes trials, substantial residual risk cardiovascular events remains. Atherosclerosis is a chronic inflammatory disease with oxidative stress playing a critical role. Oxidative modification of apoB containing lipoproteins enhances internalization leading to foam cell formation. In addition, oxidized LDL induces inflammation, immune cell activation, and cellular toxicity. HDL protects against atherosclerosis via multiple roles including promoting cholesterol efflux, preventing LDL oxidation, maintaining endothelial barrier function, and by minimizing cellular oxidative stress and inflammation. HDL-C concentration is inversely associated with cardiovascular disease (CVD), but recent studies suggest that assays of HDL function may provide new independent markers for CVD risk. Evidence has mounted that oxidative modification of HDL compromises its functions, and studies suggest that oxidized HDL is indeed proatherogenic.

During lipid peroxidation, highly reactive dicarbonyls, including 4-oxo-nonenal (4-ONE) malondialdehyde (MDA) and isolevuglandins (IsoLGs) are formed. These reactive lipid dicarbonyls covalently bind to DNA, proteins, and phospholipid causing alterations in lipoprotein and cellular functions. In particular, modification with reactive lipid dicarbonyls promotes inflammatory responses and toxicity that may be relevant to atherosclerosis. Present inventors identified 2-hydroxylbenzylamine (2-HOBA) as a highly reactive aldehyde scavenger that selectively reacts with IsoLG and closely related dicarbonyls. Indeed, present inventors have shown that 2-HOBA protects against oxidative stress associated hypertension, oxidant induced cytotoxicity, neurodegeneration and rapid pacing induced amyloid oligomer formation. While there is evidence that reactive aldehydes play a role in atherogenesis, to date the effects of aldehyde scavenging on the development of atherosclerosis have not been examined.

Identifying effective strategies to assess the contribution of reactive lipid dicarbonyls to disease processes in vivo has been challenging. Although formation of reactive lipid dicarbonyls theoretically could be suppressed simply by lowering levels of reactive oxygen species (ROS) using dietary antioxidants, the use of antioxidants to prevent atherosclerotic cardiovascular events has proven problematic with most clinical outcomes trials failing to show a benefit. Dietary antioxidants like vitamin C and vitamin E are relatively ineffective suppressors of oxidative injury and lipid peroxidation. In fact, careful studies of patients with hypercholesterolemia found that the doses of vitamin E required to significantly reduce lipid peroxidation were substantially greater than those typically used in most clinical trials. Furthermore, the high doses of antioxidants needed to suppress lipid peroxidation have been associated with significant adverse effects, likely because ROS play critical roles in normal physiology including protection against bacterial infection and in a number of cell signaling pathway. Finally, for discovery purposes, the use of antioxidants provides little information about the role of reactive lipid carbonyls because suppression of ROS inhibits formation of a broad spectrum of oxidatively modified macromolecules besides reactive lipid carbonyl species.

An alternative approach to broad suppression of ROS utilizing antioxidants is to use small molecule scavengers that selectively react with lipid dicarbonyl species without altering ROS levels, thereby preventing lipid dicarbonyls from modifying cellular macromolecules without disrupting normal ROS signaling and function. 2-hydroxybenzylamine (2-HOBA) (salicylamine) rapidly reacts with lipid dicarbonyls such as IsoLG, ONE, and MDA, but not with lipid monocarbonyls such as 4-hydroxynonenal. The 2-HOBA isomer 4-hydroxybenzylamine (4-HOBA) is ineffective as a dicarbonyl scavenger. Both of these compounds are orally bioavailable, so they can be used to examine the effects of lipid dicarbonyl scavenging in in vivo. 2-HOBA protects against oxidative stress associated hypertension, oxidant induced cytotoxicity, neurodegeneration and rapid pacing induced amyloid oligomer formation. While there is evidence that reactive lipid dicarbonyls play a role in atherogenesis, to date the effects of scavenging lipid dicarbonyl on the development of atherosclerosis have not been examined.

The present inventors have discovered that treatment with compounds of the present invention, including 2-HOBA, for example, significantly attenuates atherosclerosis development in hypercholesterolemic $Ldlr^{-/-}$ mice. More importantly, treatment with compounds of the present invention inhibits lesion cell death and necrotic core formation leading to more stable plaque formation as evidenced by increased lesion collagen content and fibrous cap thickness. Consistent with the decrease in atherosclerosis from 2-HOBA treatment being due to scavenging of reactive aldehydes, the atherosclerotic lesion MDA content was markedly reduced in 2-HOBA treated versus control mice. The present inventors further show that 2-HOBA treatment results in decreased plasma MDA-LDL and MDA-HDL. In addition, MDA-apoAI adduct formation was decreased, and importantly, 2-HOBA treatment caused more efficient HDL function in reducing macrophage cholesterol stores. Thus, scavenging of reactive carbonyls with 2-HOBA has multiple antiatherogenic therapeutic effects that likely contribute to its ability to reduce the development of atherosclerosis in hypercholesterolemic $Ldlr^{-/-}$ mice.

Examples of compounds of the present invention include, but are not limited to, compounds selected from the formula or analogs thereof, and pharmaceutical salts thereof, and their use as anti-atherosclerosis agents:

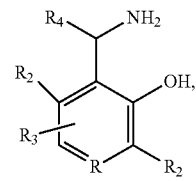

wherein:
R is N or C;
$R_2$ is independently H, substituted or unsubstituted alkyl;
$R_3$ is H, halogen, alkoxy, hydroxyl, nitro;
$R_4$ is H, substituted or unsubstituted alkyl, carboxyl; or analogs thereof.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

As used herein, the term "subject" refers to a target of administration. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed. As can be seen herein, there is overlap in the definition of treating and preventing.

As used herein, the term "diagnosed" means having been subjected to a physical examination by a person of skill, for example, a physician, and found to have a condition that can be diagnosed or treated by the compounds, compositions, or methods disclosed herein. As used herein, the phrase "identified to be in need of treatment for a disorder," or the like, refers to selection of a subject based upon need for treatment of the disorder. For example, a subject can be identified as having a need for treatment of a disorder (e.g., a disorder related to inflammation) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "scavenger" or "scavenging" refers to a chemical substance that can be administered in order to remove or inactivate impurities or unwanted reaction products. For example, the isoketals irreversibly adduct specifically to lysine residues on proteins. The isoketal scavengers of the present invention react with isoketals before they adduct to the lysine residues. Accordingly, the compounds of the present invention "scavenge" isoketals, thereby preventing them from adducting to proteins.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by a formula $—(CH_2)_a—$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $—OA^1$ where $A^1$ is alkyl or cycloalkyl as defined above. "Alkoxy" also includes polymers of alkoxy groups as just described; that is, an alkoxy can be a polyether such as $—OA^1-OA^2$ or $—OA^1-(OA^2)_a-OA^3$, where "a" is an integer of from 1 to 200 and $A^1$, $A^2$, and $A^3$ are alkyl and/or cycloalkyl groups.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

The term "hydroxyl" as used herein is represented by a formula —OH.

The term "nitro" as used herein is represented by a formula $—NO_2$.

The term "pharmaceutically acceptable" describes a material that is not biologically or otherwise undesirable, i.e., without causing an unacceptable level of undesirable biological effects or interacting in a deleterious manner.

As stated above, one embodiment of the present invention is a method of treating, preventing, or ameliorating atherosclerosis by treatment with γ-KA scavengers, and preferably with the γ-KA scavengers of the present invention.

Embodiments of the present invention include compounds of the following formula, and their use as anti-atherosclerotic agents:

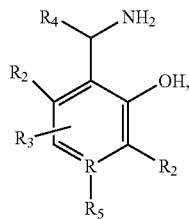

wherein:
R is N or C;
$R_2$ is independently H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_2$, $R_3$ and $R_4$, and may cyclize with to one or more $R_2$, $R_3$, or $R_5$ to form an optionally substituted $C_{3-8}$ membered ring containing C, O, S or N;
$R_3$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$ or $R_5$ to form an optionally substituted $C_{3-8}$ membered ring containing C, O, S or N;
$R_4$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_5$ to form an optionally substituted $C_{3-8}$ membered ring containing C, O, S or N;
$R_5$ is a bond, H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N;
and stereoisomers and analogs thereof.

Embodiments of the present invention also include compounds of the following formula, and their use as anti-atherosclerotic agents:

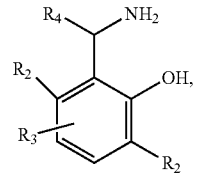

wherein:
$R_2$ is independently H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_2$, $R_3$ and $R_4$, and may cyclize with to one or more $R_2$, $R_3$, or $R_5$ to form an optionally substituted $C_{3-8}$ membered ring containing C, O, S or N;
$R_3$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$ or $R_5$ to form an optionally substituted $C_{3-8}$ membered ring containing C, O, S or N;
$R_4$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_5$ to form an optionally substituted $C_{3-8}$ membered ring containing C, O, S or N;
$R_5$ is a bond, H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N;
and stereoisomers and analogs thereof.

In other embodiments of the present invention, examples of compounds of the present invention include, but are not limited to, compounds selected from the following formula or analogs thereof, and pharmaceutical salts thereof, and their use as agents described herein:

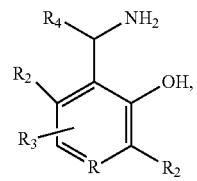

wherein:
R is N or C;
$R_2$ is independently H, substituted or unsubstituted alkyl;
$R_3$ is H, halogen, alkoxy, hydroxyl, nitro;
$R_4$ is H, substituted or unsubstituted alkyl, carboxyl; and stereoisomers and analogs thereof.

In another embodiment of the present invention is a compound selected from the above formula or analogs thereof, and pharmaceutical salts thereof, and their use as anti-atherosclerotic agents, provided that $R_2$ is not —$CH_2$—OH when R is N, $R_4$ is H, and $R_2$ is $CH_3$.

The compounds or analogs may chosen from:

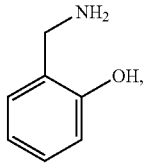

or an analog thereof.

The compounds or analogs may also be chosen from:

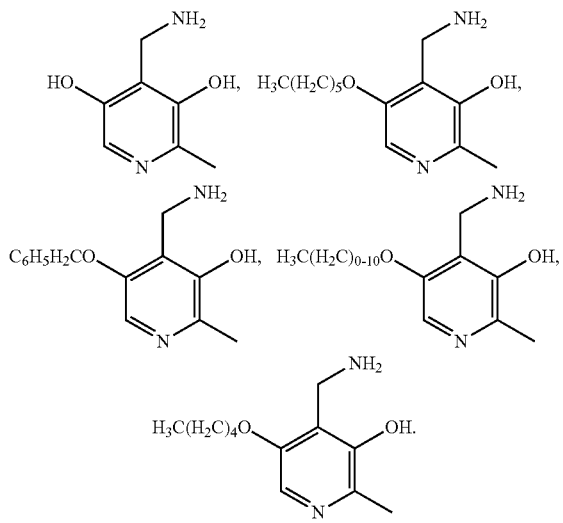

or an analog thereof.

The compounds or analogs may also be chosen from:

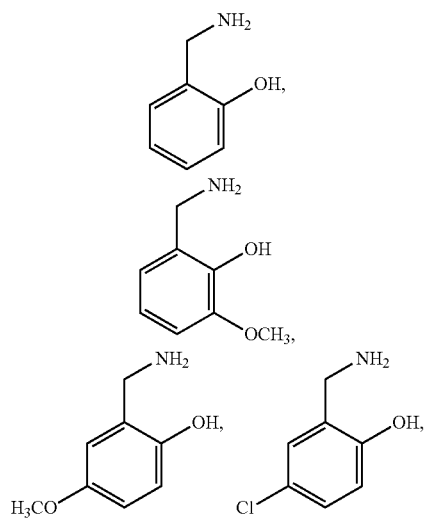

-continued

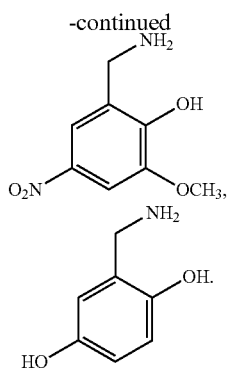

or an analog thereof.

The compounds may also be chosen from:

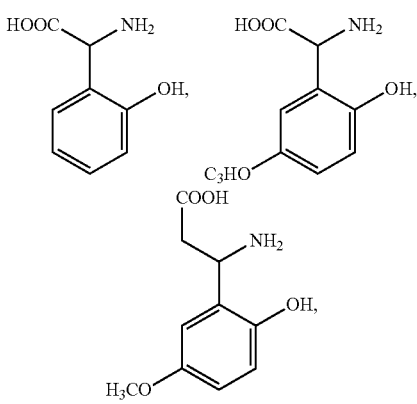

or an analog thereof.

The compounds may also be chosen from

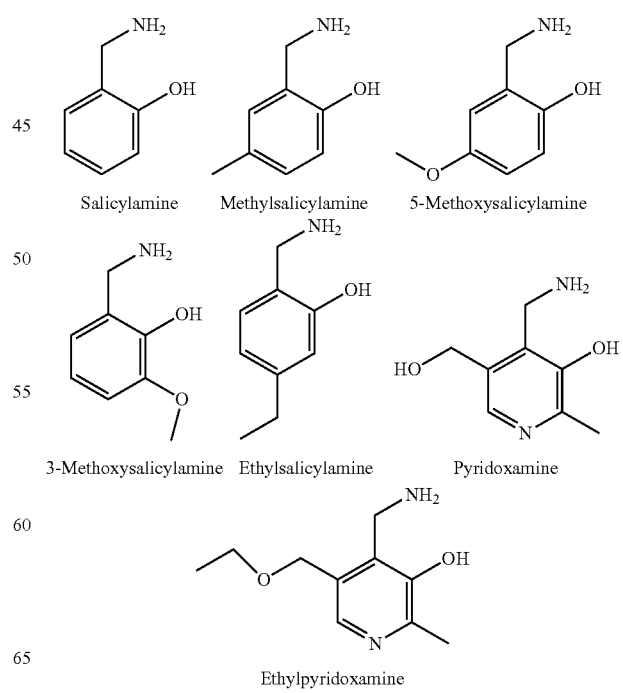

Salicylamine  Methylsalicylamine  5-Methoxysalicylamine

3-Methoxysalicylamine  Ethylsalicylamine  Pyridoxamine

Ethylpyridoxamine

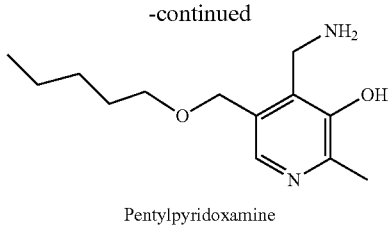

Pentylpyridoxamine or an analog thereof.

Another embodiment of the present invention is a compound for use in treating, preventing, or ameliorating atherosclerosis, wherein the compound has a structure represented by the following formula:

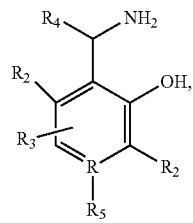

wherein:

R is N or C;

$R_2$ is independently H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_2$, $R_3$ and $R_4$, and may cyclize with to one or more $R_2$, $R_3$, or $R_5$ to form an optionally substituted $C_{3-8}$ membered ring containing C, O, S or N;

$R_3$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$ or $R_5$ to form an optionally substituted $C_{3-8}$ membered ring containing C, O, S or N;

$R_4$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_5$ to form an optionally substituted $C_{3-8}$ membered ring containing C, O, S or N;

$R_5$ is a bond, H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N;

and stereoisomers and analogs thereof.

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In other aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids" includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds. The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention can comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

The compounds of the present invention can be administered as the sole active pharmaceutical agent, or can be used in combination with one or more other agents useful for treating or preventing various complications, such as, for example, atherosclerosis-related diseases. When administered as a combination, the therapeutic agents can be formulated as separate compositions that are given at the same time or different times, or the therapeutic agents can be given as a single composition.

As indicated herein, the compounds of the present invention may be made up in a solid form (including granules, powders or suppositories) or in a liquid form (e.g., solutions, suspensions, or emulsions). They may be applied in a variety of solutions and may be subjected to conventional pharmaceutical operations such as sterilization and/or may contain conventional adjuvants, such as preservatives, stabilizers, wetting agents, emulsifiers, buffers etc.

Thus, for administration, the compounds of the present invention are ordinarily combined with one or more adjuvants appropriate for the indicated route of administration. For example, they may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinylpyrrolidine, and/or polyvinyl alcohol, and tableted or encapsulated for conventional administration. Alternatively, they may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

In therapeutic applications, the compounds of the present invention may be administered to a mammalian patient in an amount sufficient to reduce or inhibit the desired indication. Amounts effective for this use depend on factors including, but not limited to, the route of administration, the stage and severity of the indication, the general state of health of the mammal, and the judgment of the prescribing physician. The compounds of the present invention are safe and effective over a wide dosage range. However, it will be understood that the amounts of pyridoxamine actually administered will be determined by a physician, in the light of the above relevant circumstances.

Pharmaceutically acceptable acid addition salts of the compounds suitable for use in methods of the invention include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfate, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glutamine, etc. (see, e.g., Berge et al., J. Pharmaceutical Science, 66: 1-19 (1977).

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Subjects, particularly individuals at high risk of developing atherosclerosis, may be treated by administering one or more of the compounds described above. As previously mentioned, the exact dosage will depend upon the particular compound being given and will be determined using procedures well known in the art, balancing toxicity and therapeutic efficacy. Compounds may also be given to test animals to study their effect on the development of atherosclerotic plaques. In these cases, dosages are limited only by toxicity. It should also be recognized that inhibitory compounds may be administered as the sole active agents in a dosage form, or they may be combined with other drugs to improve overall effectiveness.

Thus, another embodiment of the present invention is a composition for use in treating, preventing, or ameliorating atherosclerosis, wherein the composition comprises a compound with a structure represented by the following formula:

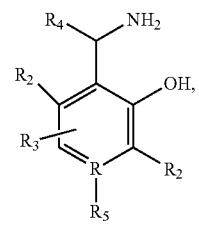

wherein:

R is N or C;

$R_2$ is independently H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_2$, $R_3$ and $R_4$, and may cyclize with to one or more $R_2$, $R_3$, or $R_5$ to form an optionally substituted $C_{3-8}$ membered ring containing C, O, S or N;

$R_3$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$ or $R_5$ to form an optionally substituted $C_{3-8}$ membered ring containing C, O, S or N;

$R_4$ is H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_5$ to form an optionally substituted $C_{3-8}$ membered ring containing C, O, S or N;

$R_5$ is a bond, H, hydroxy, halogen, nitro, $CF_3$, $C_{1-6}$ alkyl, $C_{1-6}$ alkoxy, $C_{3-10}$ cycloalkyl, $C_{3-8}$ membered ring containing C, O, S or N, optionally substituted with one or more $R_4$, $R_2$ and $R_3$ may cyclize with to one or more $R_2$, $R_3$, or $R_4$ to form an optionally substituted $C_{3-8}$ membered ring containing C, O, S or N;

and stereoisomers and analogs thereof; and a pharmaceutically acceptable carrier.

EXAMPLES

In addition to examples shown above, the following examples demonstrate certain embodiments of the present invention. All examples are to be construed as being exemplary of certain aspects of the present invention and are not to be construed as being limiting thereof.

Abbreviations: 2-HOBA, 2-hydroxybenzylamine; 4-HOBA, 4-hydroxybenzylamine; MDA, malondialdehyde; 4-HNE, 4-hydroxynonenal; IsoLGs, isolevuglandins; HDL, high-density lipoproteins; LDL, low-density lipoprotein; LDLR, low-density lipoprotein receptor; ApoAI, apolipoprotein AI; ApoB, apolipoprotein B; ROS, reactive oxygen species; IL, interleukin.

Materials and Methods:

Mice: $Ldlr^{-/-}$ and WT on C57BL/6 background mice were obtained from the Jackson Laboratory. Animal protocols were performed according to the regulations of Vanderbilt University's Institutional Animal Care and Usage Committee. Mice were maintained on chow or a Western-type diet containing 21% milk fat and 0.15% cholesterol (Teklad). Eight week old, female mice were pretreated mice with vehicle alone (Water) or containing either 1 g/L of 4-HOBA or 1 g/L of 2-HOBA. After two weeks, the mice continued to receive treatment and were administered a Western diet for 16 weeks to induce hypercholesterolemia and atherosclerosis.

Cell Culture: Peritoneal macrophages were isolated from mice 72 hours post injection of 3% thioglycollate and maintained in DMEM plus 10% fetal bovine serum (FBS, Gibco) as previously described. Human aortic endothelial cells (HAECs) were obtained from Lonza and maintained in endothelial cell basal medium-2 plus 1% FBS and essential growth factors (Lonza).

HDL Isolation from Mouse Plasma and Measurement of HDL Capacity to Reduce Macrophage Cholesterol: HDL was isolated from mouse plasma using HDL Purification Kit (Cell BioLabs, Inc.) following the manufacturer's protocol. Briefly, apoB containing lipoproteins and HDL were sequentially precipitated with dextran sulfate. The HDL was then resuspended and washed. After removing the dextran sulfate, the HDL was dialyzed against PBS. To measure the capacity of the HDL to reduce macrophage cholesterol, apoE$^{-/-}$ macrophages were cholesterol enriched by incubation for 48 h in DMEM containing 100 µg protein/ml of acetylated LDL. The cells were then washed, and incubated for 24 h in DMEM alone or with 25 µg HDL protein/ml. Cellular cholesterol was measured before and after incubation with HDL using an enzymatic cholesterol assay as described.

Measurement of MDA-LDL, MDA-HDL, and MDA-ApoAI: Sandwich ELISA was used to measure plasma MDA-LDL and MDA-HDL levels following the manufacturer's instructions (Cell BioLabs, Inc.). Briefly, isolated LDL or HDL samples and MDA-HDL standards were added onto anti-MDA coated plates, and after blocking, the samples were incubated with biotinylated anti-apoB or anti-ApoAI primary antibody. The samples were then incubated for 1 h with streptavidin-enzyme conjugate and 15 min with substrate solution. After stopping the reaction, the O.D. was measured at 450 nm wavelength. MDA-ApoAI was detected in mouse plasma by immunoprecipitation of ApoAI and western blotting. Briefly, 50 µl of mouse plasma were prepared with 450 µL of IP Lysis Buffer (Pierce) plus 0.5% protease inhibitor mixture (Sigma), and immunoprecipitated with 10 µg of polyclonal antibody against mouse ApoAI (Novus). Then 25 µL of magnetic beads (Invitrogen) was added, and the mixture was incubated for 1 h at 4° C. with rotation. The magnetic beads were then collected, washed three times, and SDS-PAGE sample buffer with β-mercaptoethanol was added to the beads. After incubation at 70° C. for 5 min, magnetic field was applied to the Magnetic Separation Rack (New England), and the supernatant was used for detecting mouse ApoAI or MDA. For Western blotting, 30-60 µg of proteins was resolved by NuPAGE Bis-Tris electrophoresis (Invitrogen), and transferred onto nitrocellulose membranes (Amersham Bioscience). Membranes were probed with primary rabbit antibodies specific for ApoAI (Novus) or MDA (Cell signaling) and fluorescent tagged IRDye 680 (LI-COR) secondary antibody. Proteins were visualized and quantitated by Odyssey 3.0 Quantification software (LI-COR).

Modification of HDL and LDL with MDA: MDA was prepared immediately before use by rapid acid hydrolysis of maloncarbonyl bis-(dimethylacetal) as described. Briefly, 20 µL of 1 M HCl was added to 200 µL of maloncarbonyl bis-(dimethylacetal), and the mixture was incubated for 45 min at room temperature. The MDA concentration was determined by absorbance at 245 nm, using the coefficient factor 13, 700 M-1 cm-1. HDL (10 mg of protein/mL) and increasing doses of MDA (0, 0.125 mM, 0.25 mM, 0.5 mM, 1 mM) were incubated at 37° C. for 24 h in 50 mM sodium phosphate buffer (pH7.4) containing DTPA 100 µM. Reactions were initiated by adding MDA and stopped by dialysis of samples against PBS at 4° C. LDL (5 mg/mL) was modified in vitro with MDA (10 mM) in the presence of vehicle alone or with 2-HOBA at 370 C for 24 h in 50 mM sodium phosphate buffer (pH7.4) containing DTPA 100 µM. Reactions were initiated by adding MDA and stopped by dialysis of samples against PBS at 4° C. The LDL samples were incubated for 24 h with macrophages and the cholesterol content of the cells was measured using an enzymatic cholesterol assay as described.

Atherosclerosis Analyses and Cross-section Immunofluorescence Staining: The extent of atherosclerosis was examined both in Oil-Red-O-stained cross-sections of the proximal aorta and by en face analysis using the KS300 imaging system (Kontron Elektronik GmbH). For immunofluorescence staining, 5 µm cross-sections of the proximal aorta were fixed in cold acetone (Sigma), blocked in Background Buster (Innovex), incubated with indicated primary antibodies (MDA and CD68) at 4° C. for overnight. After incubation with fluorescent labeled secondary antibodies at 37 C for 1 hour, the nucleus was counter stained with Hoechst. Images were captured with a fluorescence microscope (Olympus IX81) and SlideBook 6 (Intelligent-Image) software and quantitated using ImageJ software (NIH).

In vitro Cellular Apoptosis and Analysis of Lesion Apoptosis and Efferocytosis: Cell apoptosis was induced as indicated and detected by fluorescent labeled Annexin V staining and quantitated by either Flow Cytometry (BD 5 LSRII) or counting Annexin V positive cells in images captured under a fluorescent microscope. The apoptotic cells in atherosclerotic lesion were measured by TUNEL staining of cross-sections of atherosclerotic proximal aorta as previously described. The TUNEL positive cells not associated with live macrophages were considered free apoptotic cells and macrophage-associated apoptotic cells were considered phagocytosed as a measure of lesion efferocytosis as previously described.

Masson's Trichrome Staining: Masson's Trichrome Staining was applied for measurement of atherosclerotic lesion collagen content, fibrous cap thickness and necrotic core size following the manufacture's instruction (Sigma) and as previously described. Briefly, 5 µm cross-sections of proximal atherosclerotic aorta root were fixed with Bouin's solution, stained with hematoxylin for nuclei (black), biebrich scarlet and phosphotungstic/phosphomolybdic acid for cytoplasm (red), and aniline blue for collagen (blue). Images were captured and analyzed for collagen content, atherosclerotic cap thickness and necrosis core by ImageJ software as described earlier.

RNA Isolation and Real-Time RT-PCR: Total RNA was extracted and purified using *Aurum* Total RNA kit (Bio-Rad) according to the manufacturer's protocol. Complementary DNA was synthesized with iScript reverse transcriptase (Bio-Rad). Relative quantitation of the target mRNA was performed using specific primers, SYBR probe (Bio-Rad), and iTaqDNA polymerase (Bio-Rad) on IQ5 thermocylcer (Bio-Rad) and normalized with 18S, as described earlier. 18S, IL-1β and TNF-α primers used were as described earlier.

Statistics: Data are presented as mean±SEM. The normality of the sample populations was examined by the Kolmogorov-Smirnov test, then differences between mean values were determined by one-way ANOVA (Bonferroni's post-test), Kruskal-Wallis test (Bunn's multiple comparison), Mann-Whitney test, and Student's t-test using GraphPad PRISM. Significance was set for $p<0.05$.

Results:

2-HOBA treatment attenuates atherosclerosis without altering plasma cholesterol in $Ldlr^{-/-}$ mice: $Ldlr^{-/-}$ mice were fed a western diet for 16 weeks and were continuously treated with vehicle alone (water) or water containing either 2-HOBA or 4-HOBA, a nonreactive analogue. Treatment with 2-HOBA reduced the extent of proximal aortic atherosclerosis was reduced by 31.1% and 31.5%, compared to treatment with either vehicle or 4-HOBA, respectively (FIGS. 1A and 1B). In addition, en face analysis of the aorta demonstrates that treatment of $Ldlr^{-/-}$ mice with 2-HOBA reduced the atherosclerosis by 60.3% and 59.1% compared to administration of vehicle and 4-HOBA, respectively (FIGS. 1C and 1D). Compared to administration of vehicle or 4-HOBA, 2-HOBA treatment did not affect the body weight (Data not shown). In addition, the plasma total cholesterol and triglyceride levels were not significantly different between the 3 groups of mice (FIG. 1E). Thus, for the first time the present inventors demonstrate that 2-HOBA treatment significantly decreases atherosclerosis development in an experimental mouse model without changing plasma cholesterol and triglyceride levels. Consistent with the 2-HOBA effects on atherosclerosis being due to aldehyde scavenging, the MDA levels in the proximal aorta were reduced by 68.5% and 66.8% in 2-HOBA treated mice compared to mice treated with vehicle alone or 4-HOBA (FIGS. 2A and 2B).

2-HOBA treatment promotes formation of more stable atherosclerotic plaques in hypercholesterolemic $Ldlr^{-/-}$ mice: As vulnerable plaques exhibit higher risk for acute cardiovascular events, the present inventors examined the effects of 2-HOBA treatment on plaque stabilization by quantitating the atherosclerotic lesion collagen content, fibrous cap thickness and necrotic core (FIGS. 3A-3D). Compared to administration of vehicle or 4-HOBA, 2-HOBA treatment increased the collagen content of the proximal aorta by 2.7- and 2.6-fold respectively (FIGS. 3A and 3B). In addition, the fibrous cap thickness was 2.31- and 2.29-fold greater in lesions of 2-HOBA treated mice versus vehicle and 4-HOBA treated mice (FIGS. 3A and 3C). Importantly, the % necrotic area in the proximal aorta was decreased by 74.8% and 73.5% in mice treated with 2-HOBA versus vehicle and 4-HOBA (FIGS. 3A and 3D). Taken together, these data show that 2-HOBA suppresses vulnerable plaque formation in the hypercholesterolemic $Ldlr^{-/-}$ mice.

2-HOBA treatment promotes cell survival and efferocytosis and reduces inflammation: As enhanced cell death and insufficient efferocytosis promote necrotic core formation and destabilization of atherosclerotic plaques, the present inventors next examined the effects of 2-HOBA treatment on cell death and efferocytosis in atherosclerotic lesions in the proximal aorta (FIGS. 4A-4D). Compared to treatment with either vehicle or 4-HOBA, the number of TUNEL positive cells was reduced by 72.9% and 72.4% in the proximal aortic lesion of 2-HOBA treated mice (FIGS. 4A and 4C). Consistent with reactive lipid dicarbonyl scavenging maintaining efficient efferocytosis, the number of TUNEL positive cells not associated with macrophages was increased by 1.9- and 2.0-fold in lesions of mice treated with vehicle and 4-HOBA versus 2-HOBA (FIGS. 4B and 4D). In vitro examination of dicarbonyl scavenging with 2-HOBA on the susceptibility of macrophages and endothelial cells to apoptosis in response to $H_2O_2$ treatment demonstrates that compared to incubation with vehicle or 4-HOBA, 2-HOBA markedly decreased the number of apoptotic cells in both macrophage and endothelial cell cultures (FIGS. 5A and 5B). In addition, 2-HOBA treatment significantly reduced the macrophage inflammatory response to oxidized LDL as shown by the decreased mRNA levels IL-1β IL-6 and TNF-α (FIGS. 5C-5E). Similar results in macrophage inflammatory response to $H_2O_2$ were observed with 2-HOBA versus vehicle or 4-HOBA treatment (FIGS. 5F-5H). Taken together, these data show that 2-HOBA treatment maintains efficient efferocytosis in vivo and prevents apoptosis and inflammation in response to oxidative stress.

Figure 6:
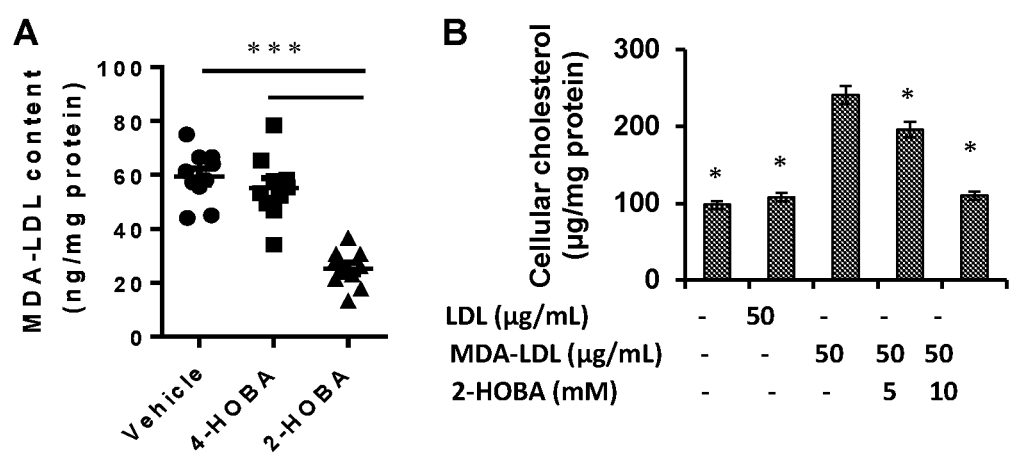
FIGS. 6A-6B show the effects of 2-HOBA on MDA modification of LDL (FIG. 6A) MDA-LDL adducts were measured by ELISA in $Ldlr^{-/-}$ mice consuming a western diet for 16 weeks and treated with 2-HOBA, 4-HOBA, or vehicle. N=10 per group, *** p<0.001.

Effects of 2-HOBA on MDA modification and function of lipoproteins and the impact of familial hypercholesterolemia on lipoprotein MDA adduct content and function: As LDL modification enhances foam cell formation, the present inventors examined the effects of in vivo dicarbonyl scavenging on plasma MDA-LDL content (FIG. 6A). Compared to treatment with either vehicle or 4-HOBA, the plasma MDA-LDL levels were reduced by 57% and 54% in $Ldlr^{-/-}$ mice treated with 2-HOBA (FIG. 6A). In addition, dicarbonyl scavenging with 2-HOBA versus vehicle during in vitro modification of LDL with MDA reduced the ability of the LDL to increase cholesterol accumulation in macrophages (FIG. 6B). Examination of the plasma MDA-LDL content of control versus homozygous FH subjects revealed that FH patients had increased MDA-LDL adducts. As oxidative modification of HDL impairs its functions, the present inventors next examined the effects of 2-HOBA treatment on HDL MDA content and function. Treatment of $Ldlr^{-/-}$ mice with 2-HOBA reduced the plasma MDA-HDL levels by 57% and 56% (FIG. 7A) compared to treatment with either vehicle or 4-HOBA. Next, the present inventors examined ApoAI MDA adduct formation by immunoprecipitating apoAI from plasma and western blotting with an antibody to MDA. After 16 weeks on the western-type diet, $Ldlr^{-/-}$ mice treated with vehicle or 4-HOBA had markedly increased plasma levels of MDA-apoAI and reduced plasma apoAI levels compared to $Ldlr^{-/-}$ mice consuming a chow diet (FIGS. 7B and 7C). In contrast, treatment of $Ldlr^{-/-}$ mice consuming a western diet with 2-HOBA dramatically reduced plasma MDA-apoAI adducts and increased apoAI levels (FIGS. 7B and 7C). Importantly, the HDL isolated from 2-HOBA treated $Ldlr^{-/-}$ mice was 2.2- and 1.7-fold more efficient at reducing cholesterol stores in ApoE−/− macrophage foam cells versus vehicle and 4-HOBA treated mice (FIG. 7D). Consistent with dicarbonyl modification of HDL playing a role in compromising HDL function, in vitro modification of HDL with MDA impaired the ability of HDL to reduce the cholesterol content of macrophage foam cells in a dose dependent manner (FIG. 7E). Importantly, plasma from human subjects with homozygous FH pre- and post-LDL apheresis (LA) had 5.9-fold and 5.6-fold more MDA-HDL adducts compared to control plasma (FIG. 7F). In addition, HDL from FH versus control subjects lacked the ability to reduce the cholesterol content of cholesterol-enriched ApoE−/− macrophages (FIG. 7G). Taken together, dicarbonyl scavenging with 2-HOBA prevents macrophage foam cell formation by reducing modification of LDL by dicarbonyls and by improving HDL net cholesterol efflux capacity. In addition, these examples show that scavenging of reactive lipid dicarbonyls with embodiments of the present invention is a therapeutic approach in humans given that LDL and HDL from subjects with homozygous FH contain increased MDA and enhance foam cell formation.

Figure 2:
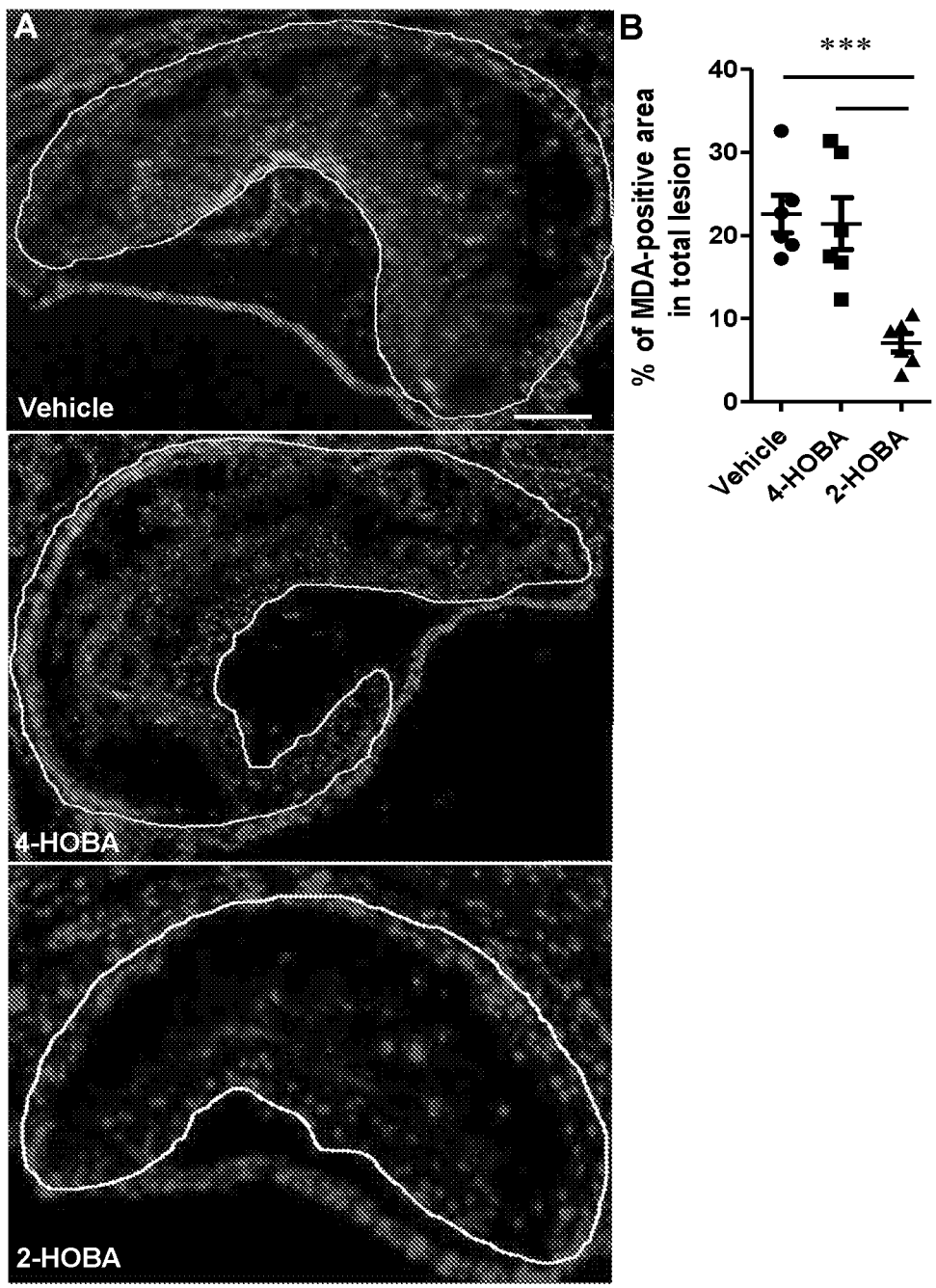
FIGS. 2A-2B show that 2-HOBA decreases the MDA content of proximal aortic atherosclerotic lesions in Ldlr$^{-/-}$ mice. MDA was detected by immunofluorescence using anti-MDA primary antibody and fluorescent-labeled secondary antibody. Nuclei were counter stained with Hoechst (Blue).
Figure 3:
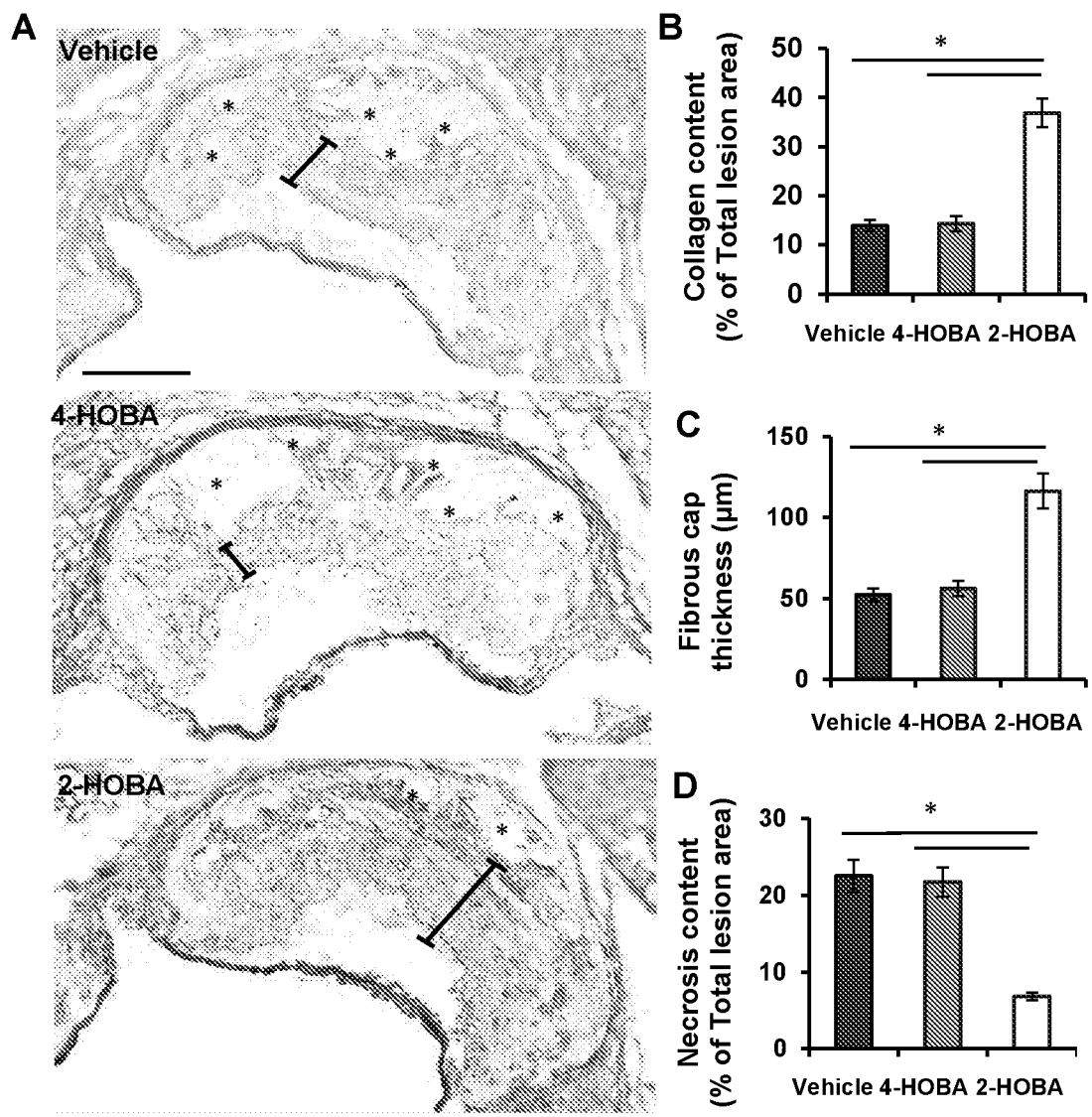
FIGS. 3A-3D show that 2-HOBA promotes stabile atherosclerotic plaque formation in $Ldlr^{-/-}$ mice. Masson's Trichrome stain was applied to analyze atherosclerotic lesion stability in proximal aorta sections of $Ldlr^{-/-}$ mice.
Figure 7:
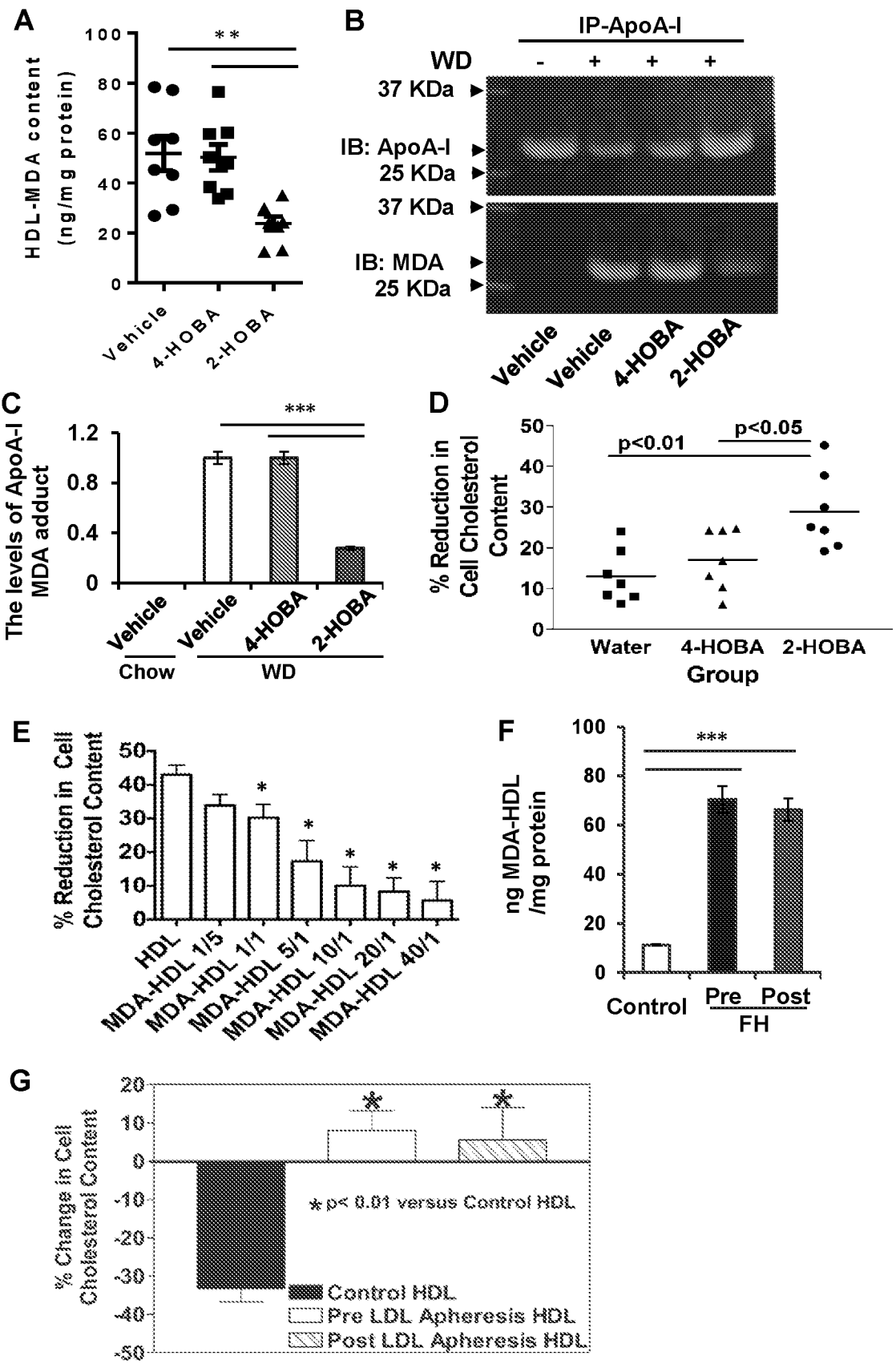
FIGS. 7A-7G show the effects of 2-HOBA and HDL-MDA adduct formation on HDL function.

Discussion:

Oxidative stress-induced lipid peroxidation has been implicated in the development of atherosclerosis. Genetic defects and/or environmental factors cause an imbalance between oxidative stress and the ability of the body to counteract or detoxify the harmful effects of oxidation products. The large body of experimental evidence implicating an important role of lipid peroxidation in the pathogenesis of atherosclerosis has stimulated tremendous interest in the potential for antioxidants to prevent atherosclerotic cardiovascular disease. Although a few trials of dietary antioxidants in humans demonstrated reductions in atherosclerosis and cardiovascular events, the majority of large clinical outcomes trials with antioxidants have failed to show any benefit in terms of reduced cardiovascular events. Possible reasons for the failure of these trials to reduce cardiovascular events, include inadequate doses of antioxidants being used in the trials and the inhibition of normal ROS signaling that may be anti-atherogenic. Treatment with scavengers of reactive dicarbonyl species derived from lipid peroxidation represents a novel alternative therapeutic strategy that will inhibit the adverse effects of ROS without destroying normal signaling by mediated by ROS In the current study, the present inventors sought to examine to potential of a new class of antioxidant, the reactive lipid dicarbonyl scavenger, to prevent the development of atherosclerosis in $Ldlr^{-/-}$ mice. Peroxidation of lipids in tissues/cells or in blood produces a number of highly reactive dicarbonyls that include malondialdehyde, isolevuglandins and 4-oxo-nonenal. These electrophiles can covalently bind to DNA, proteins, and phospholipid causing alterations in lipoprotein and cellular functions. The present inventors are the first to examine the effects of aldehyde scavenging on atherosclerosis, and the present inventors demonstrate that 2-HOBA, a reactive aldehyde scavenger, significantly reduces atherosclerosis development in the hypercholesterolemic $Ldlr^{-/-}$ mouse model (FIG. 1). Importantly, our studies show that 2-HOBA treatment markedly improves features of the stability of the atherosclerotic plaque as evidenced by decreased necrosis and increased fibrous cap thickness and collagen content (FIG. 3). Thus, aldehyde scavenging using 2-HOBA offers therapeutic potential in reducing risk of clinical events resulting from formation of vulnerable atherosclerotic plaques. Furthermore, dicarbonyl scavenging reduced in vivo MDA modification of HDL, thereby improving its net cholesterol efflux capacity (FIG. 7). In addition, MDA modification was increased in FH-HDL, which likely contributed to the enhanced foam cell formation induced by their HDL (FIG. 7). Taken together, dicarbonyl scavenging using 2-HOBA offers therapeutic benefit in reducing atherosclerosis development and the risk of clinical events resulting from formation of vulnerable atherosclerotic plaques.

Embodiments of the present invention demonstrate that 2-HOBA reduces atherosclerosis development without decreasing plasma cholesterol levels (FIG. 1). Without being bound by theory or mechanism, the atheroprotective effects of 2-HOBA are likely due to scavenging bioactive dicarbonyls. That the effects of 2-HOBA are mediated by their action as dicarbonyl scavengers is further supported by the finding that 4-HOBA, a geometric isomer of 2-HOBA, which is not a scavenger is not atheroprotective. Prevention of atherosclerosis by removing dicarbonyls substantially strengthens the hypothesis that these dicarbonyls contribute to the pathogenesis of atherogenesis.

HDL mediates a number of atheroprotective functions and evidence has mounted that markers of HDL dysfunction, such as impaired cholesterol efflux capacity, may be a better indicator of CAD risk than HDL-C levels. Patients with FH have previously been shown to have impaired HDL cholesterol efflux capacity, indicative of dysfunctional HDL. The present inventors show that consumption of a Western diet by $Ldlr^{-/-}$ mice results in enhanced MDA-apoAI adduct formation (FIG. 7), and that 2-HOBA treatment dramatically reduces modification of both apoAI and HDL with MDA. Similarly, FH patients had increased plasma levels of MDA-HDL adducts. In addition, in vitro modification of HDL resulted in decreased net cholesterol efflux capacity, which is consistent with studies by Shao and colleagues demonstrating that modification of lipid-free apoAI with MDA blocks ABCA1 mediated cholesterol efflux. Studies have also shown that long term cigarette smoking causes increases MDA-HDL adduct formation, and smoking cessation leads to improved HDL function with increased cholesterol efflux capacity. In line with these results, we found that HDL isolated from 2-HOBA versus vehicle and 4-HOBA treated mice has enhanced capacity to reduce cholesterol stores in macrophage foam cells (FIG. 7). Furthermore, FH-HDL had markedly increased MDA adducts and severely impaired ability to reduce macrophage cholesterol stores pre- and post-LDL apheresis (FIG. 7). Thus, one of the atheroprotective mechanisms of 2-HOBA is likely through preventing formation of dicarbonyl adducts of HDL proteins, thereby preserving HDL net cholesterol efflux function. In addition to decreasing HDL oxidative modification, our studies show that 2-HOBA treatment greatly diminishes the in vivo and in vitro MDA modification of LDL. Studies have shown that MDA modification of LDL promotes foam cell formation and an inflammatory response. Importantly, neutralization of MDA-apoB adducts with antibodies greatly enhances atherosclerosis regression in human apoB100 transgenic $Ldlr^{-/-}$ mice. Thus, it is likely that the decreased atherosclerosis with 2-HOBA treatment is also due in part to decreased dicarbonyl modification of apoB.

Figure 4:
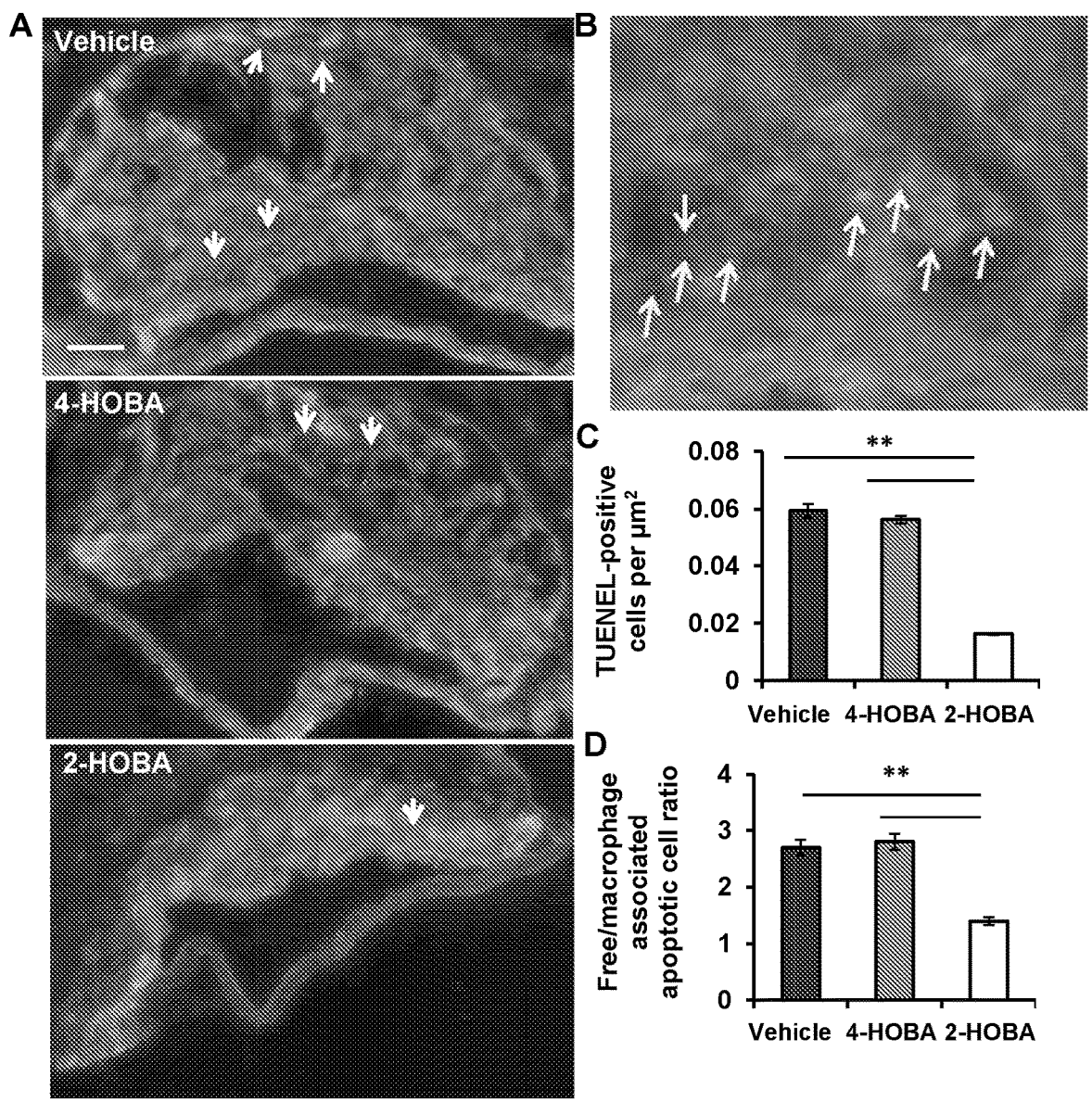
FIGS. 4A-4D show that 2-HOBA prevents cell death and increases efferocytosis in atherosclerotic lesions of the $Ldlr^{-/-}$ mice.
Figure 5:
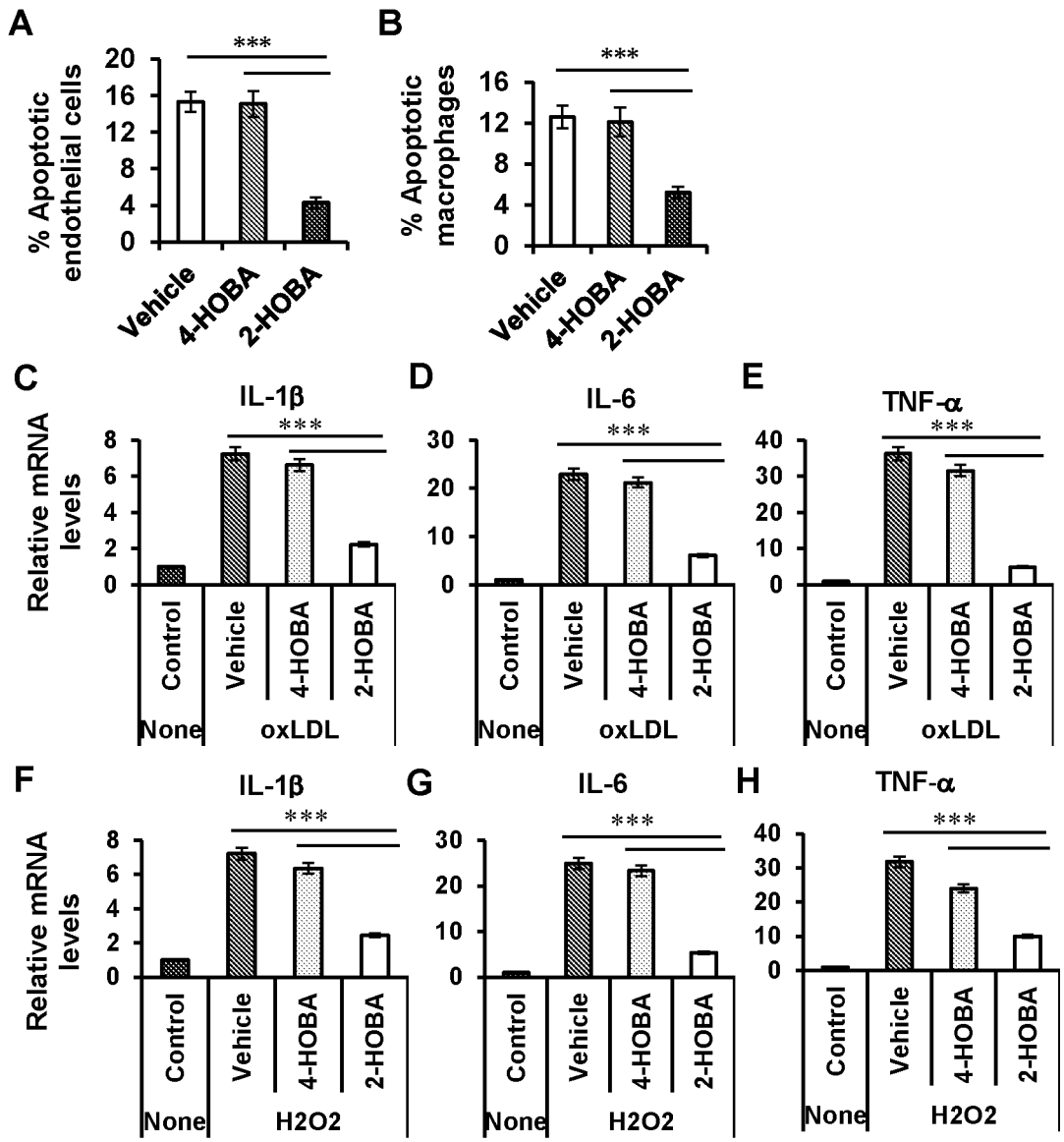
FIGS. 5A-5H show that in vitro treatment with 2-hydroxybenzylamine suppresses oxidative stress-induced the cell apoptosis and inflammation.

Evidence has mounted that increased oxidative stress in arterial intima cells is pivotal in inducing ER stress, inflammation, and cell death in atherogenesis. In particular, efficient efferocytosis and limited cell death are critical to preventing the necrosis and the excessive inflammation characteristic of the vulnerable plaque. The present inventors have demonstrated that treatment with 2-HOBA promotes characteristics of more stable atherosclerotic plaques in $Ldlr^{-/-}$ mice (FIG. 3). The present inventors have also shown that 2-HOBA treatment decreased the atherosclerotic lesion MDA adduct content (FIG. 2), supporting the ability of dicarbonyl scavenging in the arterial intima to limit oxidative stress induced cell death and destabilization of the plaque. Thus, an embodiment of the present invention is the scavenging of dicarbonyls with 2-HOBA in vitro to limit oxidative stress induced apoptosis in both endothelial cells and macrophages (FIG. 5). The decreased cell death is likely due in part to the greatly diminished inflammatory response to oxidative stress from dicarbonyl scavenging with 2-HOBA (FIG. 5). Importantly, 2-HOBA treatment as per the present invention maintained efficient efferocytosis and reduced the number of dead cells in the atherosclerotic lesions (FIG. 4). As a result, dicarbonyl scavenging with 2-HOBA promoted formation of stable plaques with decreased necrosis and enhanced collagen content and fibrous cap thickness (FIG. 3). Hence, the ability of 2-HOBA to limit death and inflammation in arterial cells in response to oxidative stress and to promote efficient efferocytosis in the artery wall provides a novel atheroprotective mechanism whereby dicarbonyl scavenging promotes features of plaque stabilization and reduces atherosclerotic lesion formation.

In conclusion, methods of the present invention suppress atherosclerosis development in hypercholesterolemic $Ldlr^{-/-}$ mice. Treatment with 2-HOBA decreased the formation of MDA-apoAI adducts thereby maintaining efficient HDL function. In addition, the prevention of MDA-apoB adducts decreases foam cell formation and inflammation. Finally, within the atherosclerotic lesion, dicarbonyl scavenging limited cell death, inflammation, and necrosis thereby effectively stabilizing the atherosclerotic plaques. As the atheroprotective effect of 2-HOBA treatment is independent of any action on plasma cholesterol levels, the present invention also meets a long felt need of therapeutically decreasing the residual CAD risk that persists in patients treated with HMG-CoA reductase inhibitors.

REFERENCES

1. Linton, M. F., Yancey, P. G., Davies, S. S., Jerome, W. G. J., Linton, E. F., and Vickers, K. C. 2000. The Role of Lipids and Lipoproteins in Atherosclerosis.
2. Sampson, U. K., Fazio, S., and Linton, M. F. 2012. Residual cardiovascular risk despite optimal LDL cholesterol reduction with statins: the evidence, etiology, and therapeutic challenges. Curr Atheroscler Rep 14:1-10.
3. Anderson, T. J. 1997. Oxidative stress, endothelial function and coronary atherosclerosis. Cardiologia 42:701-714.
4. Aviram, M. 2011. Atherosclerosis: cell biology and lipoproteins—inflammation and oxidative stress in atherogenesis: protective role for paraoxonases. Curr Opin Lipidol 22:243-244.
5. Peluso, I., Morabito, G., Urban, L., Ioannone, F., and Serafini, M. 2012. Oxidative stress in atherosclerosis development: the central role of LDL and oxidative burst. Endocr Metab Immune Disord Drug Targets 12:351-360.
6. Kontush, A., Lindahl, M., Lhomme, M., Calabresi, L., Chapman, M. J., and Davidson, W. S. 2015. Structure of HDL: particle subclasses and molecular components. Handb Exp Pharmacol 224:3-51.
7. Riwanto, M., Rohrer, L., von Eckardstein, A., and Landmesser, U. 2015. Dysfunctional HDL: from structure-function-relationships to biomarkers. Handb Exp Pharmacol 224:337-366.
8. Linton, M. F., Tao, H., Linton, E. F., and Yancey, P. G. 2017. SR-BI: A Multifunctional Receptor in Cholesterol Homeostasis and Atherosclerosis. Trends Endocrinol Metab.
9. Brewer, H. B., Jr., and Rader, D. J. 1991. HDL: structure, function and metabolism. Prog Lipid Res 30:139-144.
10. Xi, H., Akishita, M., Nagai, K., Yu, W., Hasegawa, H., Eto, M., Kozaki, K., and Toba, K. 2007. Potent free radical scavenger, edaravone, suppresses oxidative stress-induced endothelial damage and early atherosclerosis. Atherosclerosis 191:281-289.
11. Vasdev, S., Gill, V. D., and Singal, P. K. 2006. Modulation of oxidative stress-induced changes in hypertension and atherosclerosis by antioxidants. Exp Clin Cardiol 11:206-216.
12. Guo, L., Chen, Z., Amarnath, V., Yancey, P. G., Van Lenten, B. J., Savage, J. R., Fazio, S., Linton, M. F., and Davies, S. S. 2015. Isolevuglandin-type lipid aldehydes induce the inflammatory response of macrophages by modifying phosphatidylethanolamines and activating the receptor for advanced glycation endproducts. Antioxid Redox Signal 22:1633-1645.
13. Kirabo, A., Fontana, V., de Faria, A. P., Loperena, R., Galindo, C. L., Wu, J., Bikineyeva, A. T., Dikalov, S., Xiao, L., Chen, W., et al. 2014. DC isoketal-modified proteins activate T cells and promote hypertension. J Clin Invest 124:4642-4656.
14. Davies, S. S., Bodine, C., Matafonova, E., Pantazides, B. G., Bernoud-Hubac, N., Harrison, F. E., Olson, S. J., Montine, T. J., Amarnath, V., and Roberts, L. J., 2nd. 2011. Treatment with a gamma-ketoaldehyde scavenger prevents working memory deficits in hApoE4 mice. J Alzheimers Dis 27:49-59.
15. Davies, S. S., Brantley, E. J., Voziyan, P. A., Amarnath, V., Zagol-Ikapitte, I., Boutaud, O., Hudson, B. G., Oates, J. A., and Roberts, L. J., 2nd. 2006. Pyridoxamine analogues scavenge lipid-derived gamma-ketoaldehydes and protect against $H_2O_2$-mediated cytotoxicity. Biochemistry 45:15756-15767.
16. Zagol-Ikapitte, I., Sosa, L R., Oram, D., Judd, A., Amarnath, K., Amarnath, V., Stec, D., Oates, J. A., and Boutaud, O. 2015. Modification of platelet proteins by malondialdehyde: prevention by dicarbonyl scavengers. J Lipid Res 56:2196-2205.
17. Sidorova, T. N., Yermalitskaya, L. V., Mace, L. C., Wells, K. S., Boutaud, O., Prinsen, J. K., Davies, S. S., Roberts, L. J., 2nd, Dikalov, S. I., Glabe, C. G., et al. 2015. Reactive gamma-ketoaldehydes promote protein misfolding and preamyloid oligomer formation in rapidly-activated atrial cells. J Mol Cell Cardiol 79:295-302.
18. Leopold, J. A. 2015. Antioxidants and coronary artery disease: from pathophysiology to preventive therapy. Coron Artery Dis 26:176-183.
19. Roberts, L. J., 2nd, Oates, J. A., Linton, M. F., Fazio, S., Meador, B. P., Gross, M. D., Shyr, Y., and Morrow, J. D. 2007. The relationship between dose of vitamin E and suppression of oxidative stress in humans. Free Radic Biol Med 43:1388-1393.
20. Amarnath, V., Amarnath, K., Amarnath, K., Davies, S., and Roberts, L. J., 2nd. 2004. Pyridoxamine: an extremely potent scavenger of 1,4-dicarbonyls. Chem Res Toxicol 17:410-415.
21. Nakajima, T., Davies, S. S., Matafonova, E., Potet, F., Amarnath, V., Tallman, K. A., Serwa, R. A., Porter, N. A., Balser, J. R., Kupershmidt, S., et al. 2010. Selective gamma-ketoaldehyde scavengers protect Nav1.5 from oxidant-induced inactivation. J Mol Cell Cardiol 48:352-359.
22. Amarnath, V., and Amarnath, K. 2015. Scavenging 4-Oxo-2-nonenal. Chem Res Toxicol 28:1888-1890.
23. Zagol-Ikapitte, I., Amarnath, V., Bala, M., Roberts, L. J., 2nd, Oates, J. A., and Boutaud, O. 2010. Characterization of scavengers of gamma-ketoaldehydes that do not inhibit prostaglandin biosynthesis. Chem Res Toxicol 23:240-250.
24. Zagol-Ikapitte, I., Matafonova, E., Amarnath, V., Bodine, C. L., Boutaud, O., Tirona, R. G., Oates, J. A., Roberts Ii, L. J., and Davies, S. S. 2010. Determination of the Pharmacokinetics and Oral Bioavailability of Salicylamine, a Potent gamma-Ketoaldehyde Scavenger, by LC/MS/MS. Pharmaceutics 2:18-29.
25. Tao, H., Yancey, P. G., Babaev, V. R., Blakemore, J. L., Zhang, Y., Ding, L., Fazio, S., and Linton, M. F. 2015. Macrophage SR-BI mediates efferocytosis via Src/PI3K/Rac1 signaling and reduces atherosclerotic lesion necrosis. J Lipid Res 56:1449-1460.

26. Robinet, P., Wang, Z., Hazen, S. L., and Smith, J. D. 2010. A simple and sensitive enzymatic method for cholesterol quantification in macrophages and foam cells. J Lipid Res 51:3364-3369.
27. Shao, B., Pennathur, S., Pagani, I., Oda, M. N., Witztum, J. L., Oram, J. F., and Heinecke, J. W. 2010. Modifying apolipoprotein A-I by malondialdehyde, but not by an array of other reactive carbonyls, blocks cholesterol efflux by the ABCA1 pathway. J Biol Chem 285:18473-18484.
28. Hartig, S. M. 2013. Basic image analysis and manipulation in ImageJ. Curr Protoc Mol Biol Chapter 14:Unit14 15.
29. Livak, K. J., and Schmittgen, T. D. 2001. Analysis of relative gene expression data using real-time quantitative PCR and the 2(-Delta Delta C(T)) Method. Methods 25:402-408.
30. Pirinccioglu, A. G., Gokalp, D., Pirinccioglu, M., Kizil, G., and Kizil, M. 2010. Malondialdehyde (MDA) and protein carbonyl (PCO) levels as biomarkers of oxidative stress in subjects with familial hypercholesterolemia. Clin Biochem 43:1220-1224.
31. Rodenburg, J., Vissers, M. N., Wiegman, A., Miller, E. R., Ridker, P. M., Witztum, J. L., Kastelein, J. J., and Tsimikas, S. 2006. Oxidized low-density lipoprotein in children with familial hypercholerolemia and unaffected siblings: effect of pravastatin. J Am Coll Cardiol 47:1803-1810.
32. Mollazadeh, H., Carbone, F., Montecucco, F., Pirro, M., and Sahebkar, A. 2018. Oxidative burden in familial hypercholesterolemia. J Cell Physiol.
33. Rahman, T., Hamzan, N. S., Mokhsin, A., Rahmat, R., Ibrahim, Z. O., Razali, R., Thevarajah, M., and Nawawi, H. 2017. Enhanced status of inflammation and endothelial activation in subjects with familial hypercholesterolaemia and their related unaffected family members: a case control study. Lipids Health Dis 16:81.
34. Yang, C. Y., Raya, J. L., Chen, H. H., Chen, C. H., Abe, Y., Pownall, H. J., Taylor, A. A., and Smith, C. V. 2003. Isolation, characterization, and functional assessment of oxidatively modified subfractions of circulating low-density lipoproteins. Arterioscler Thromb Vasc Biol 23:1083-1090.
35. Calderon, J. C., Fernandez, A. Z., and Maria de Jesus, A. I. 2008. [Atherosclerosis, oxidative stress and physical activity. Review]. Invest Clin 49:397-410.
36. Davies, S. S., and Zhang, L. S. 2017. Reactive Carbonyl Species Scavengers-Novel Therapeutic Approaches for Chronic Diseases. Curr Pharmacol Rep 3:51-67.
37. Fisher, E. A., Feig, J. E., Hewing, B., Hazen, S. L., and Smith, J. D. 2012. High-density lipoprotein function, dysfunction, and reverse cholesterol transport. Arterioscler Thromb Vasc Biol 32:2813-2820.
38. Rohatgi, A., Khera, A., Berry, J. D., Givens, E. G., Ayers, C. R., Wedin, K. E., Neeland, I. J., Yuhanna, I. S., Rader, D. R., de Lemos, J. A., et al. 2014. HDL cholesterol efflux capacity and incident cardiovascular events. N Engl J Med 371:2383-2393.
39. Khera, A. V., Cuchel, M., de la Llera-Moya, M., Rodrigues, A., Burke, M. F., Jafri, K., French, B. C., Phillips, J. A., Mucksavage, M. L., Wilensky, R. L., et al. 2011. Cholesterol efflux capacity, high-density lipoprotein function, and atherosclerosis. N Engl J Med 364:127-135.
40. Takata, K., Imaizumi, S., Kawachi, E., Suematsu, Y., Shimizu, T., Abe, S., Matsuo, Y., Tsukahara, H., Noda, K., Yahiro, E., et al. 2014. Impact of cigarette smoking cessation on high-density lipoprotein functionality. Circ J 78:2955-2962.
41. Amaki, T., Suzuki, T., Nakamura, F., Hayashi, D., Imai, Y., Morita, H., Fukino, K., Nojiri, T., Kitano, S., Hibi, N., et al. 2004. Circulating malondialdehyde modified LDL is a biochemical risk marker for coronary artery disease. Heart 90:1211-1213.
42. Schiopu, A., Frendeus, B., Jansson, B., Soderberg, I., Ljungcrantz, I., Araya, Z., Shah, P. K., Carlsson, R., Nilsson, J., and Fredrikson, G. N. 2007. Recombinant antibodies to an oxidized low-density lipoprotein epitope induce rapid regression of atherosclerosis in apobec-1 (−/−)/low-density lipoprotein receptor(−/−) mice. J Am Coll Cardiol 50:2313-2318.
43. Tsimikas, S., Miyanohara, A., Hartvigsen, K., Merki, E., Shaw, P. X., Chou, M. Y., Pattison, J., Torzewski, M., Sollors, J., Friedmann, T., et al. 2011. Human oxidation-specific antibodies reduce foam cell formation and atherosclerosis progression. J Am Coll Cardiol 58:1715-1727.
44. Hjerpe, C., Johansson, D., Hermansson, A., Hansson, G. K., and Zhou, X. 2010. Dendritic cells pulsed with malondialdehyde modified low density lipoprotein aggravate atherosclerosis in Apoe(−/−) mice. Atherosclerosis 209:436-441.
45. Scull, C. M., and Tabas, I. 2011. Mechanisms of ER stress-induced apoptosis in atherosclerosis. Arterioscler Thromb Vasc Biol 31:2792-2797.
46. Bryk, D., Olejarz, W., and Zapolska-Downar, D. 2017. The role of oxidative stress and NADPH oxidase in the pathogenesis of atherosclerosis. Postepy Hig Med Dosw (Online) 71:57-68.
47. Tabas, I. 2007. Apoptosis and efferocytosis in mouse models of atherosclerosis. Curr Drug Targets 8:1288-1296.

The invention thus being described, it would be obvious that the same can be varied in many ways. Such variations that would be obvious to one of ordinary skill in the art is to be considered as being bard of this disclosure.

Unless otherwise indicated, all numbers expressing quantities of ingredients, properties such as reaction conditions, and so forth used in the Specification are to be understood as being modified in all instances by the term "about." Accordingly, unless indicated by the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental sections or the example sections are reported as precisely as possible. Any numerical value, however, inherently contain certain errors necessarily resulting from the standard deviation found in their respective testing measurements.

We claim:

1. A method of attenuating atherosclerosis, comprising administering to a patient in need thereof a compound of the following formula:

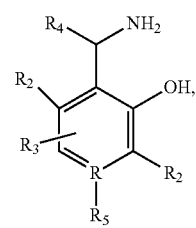

wherein:
 R is C;
 $R_2$ is independently H, $C_{1-6}$ alkyl, or $C_{1-6}$ alkoxy;
 $R_3$ is H, hydroxy, halogen, $C_{1-6}$ alkyl, $C_{1-6}$ alkoxy, or $NO_2$;
 $R_4$ is H, $C_{1-6}$ alkyl, $CH_2C(O)OH$ or $C(O)OH$;
 $R_5$ is H, or $C_{1-6}$ alkyl;
 and a pharmaceutically acceptable salt thereof.

2. The method of claim 1, wherein the compound is of the following formula:

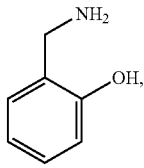

or a pharmaceutically acceptable salt thereof.

3. The method of claim 1, wherein the compound is of the following formula:

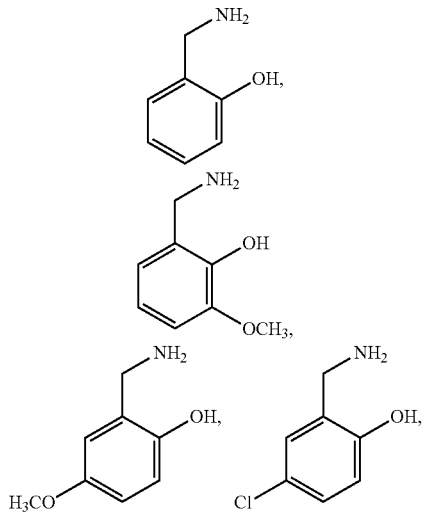

or a pharmaceutically acceptable salt thereof.

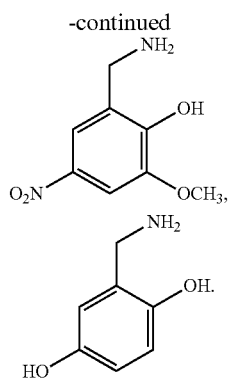

or a pharmaceutically acceptable salt thereof.

4. The method of claim 1, wherein the compound is of the following formula:

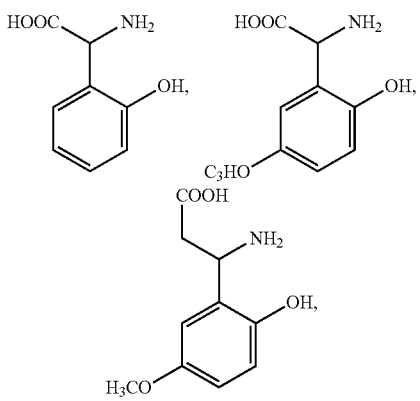

or a pharmaceutically acceptable salt thereof.

5. The method of claim 1, wherein the compound is 2-hydroxybenzylamine, methyl-2-hydroxybenzylamine, or ethyl-2-hydroxybenzylamine.

* * * * *